US00PP16688P2

(12) United States Plant Patent
Miyazaki

(10) Patent No.: US PP16,688 P2
(45) Date of Patent: Jun. 20, 2006

(54) ***SENECIO* PLANT NAMED 'SUNSENEBULBAI'**

(50) Latin Name: ***Senecio cruentus*×*Senecio heritieri***
Varietal Denomination: Sunsenebulbai

(75) Inventor: Kiyoshi Miyazaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 65 days.

(21) Appl. No.: 11/055,855

(22) Filed: Feb. 11, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Senecio* plant named 'Sunsenebulbai', characterized by its compact, upright and outwardly spreading growth habit; freely branching growth habit; freely flowering habit; long flowering period; and large inflorescences with violet blue and white bi-colored ray florets and purple-colored disc florets.

1 Drawing Sheet

Botanical designation: *Senecio cruentus*×*Senecio heritieri.*
Cultivar denomination: 'Sunsenebulbai'.

BACKGROUND OF THE INVENTION

The present invention relates to a new and distinct cultivar of *Senecio* plant, commonly referred to as Cineraria, botanically known as *Senecio cruentus*×*Senecio heritieri,* and referred to by the name 'Sunsenebulbai'.

The new *Senecio* is the product of a planned breeding program conducted by the Inventor in Yamanashi, Japan. The objective of the breeding program is to develop new compact *Senecios* with attractive ray and disc coloration.

The new *Senecio* originated from a cross-pollination made by the Inventor in January, 1995, in Yamanashi, Japan, of the *Senecio cruentus* cultivar Jupiter Blue-white, not patented, as the female, or seed, parent with an unnamed seedling selection of *Senecio heritieri*, not patented, as the male, or pollen, parent. The new *Senecio* was discovered and selected by the Inventor as a single plant within the progeny of the stated cross-pollination in a controlled environment in Yamanashi, Japan.

Asexual reproduction of the new *Senecio* by terminal vegetative cuttings in Yamanashi, Japan since March, 1996, has shown that the unique features of this new *Senecio* are stable and reproduced true to type in successive generations.

BRIEF SUMMARY OF THE INVENTION

The cultivar Sunsenebulbai has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunsenebulbai'. These characteristics in combination distinguish 'Sunsenebulbai' as a new and distinct cultivar:

1. Compact, upright and outwardly spreading growth habit.
2. Freely branching growth habit.

3. Freely flowering habit.
4. Long flowering period.
5. Large inflorescences with violet blue and white bi-colored ray florets and purple-colored disc florets.

Plants of the new *Senecio* can be compared to plants of the female parent, the cultivar Jupiter Blue-white. In side-by-side comparisons conducted in Yamanashi, Japan, plants of the new *Senecio* differed from plants of the cultivar Jupiter Blue-white in the following characteristics:

1. Plants of the new *Senecio* were taller and had longer internodes than plants of the cultivar Jupiter Blue-white.
2. Plants of the new *Senecio* had smaller leaves than plants of the cultivar Jupiter Blue-white.

Plants of the new *Senecio* can be compared to plants of the male parent selection. In side-by-side comparisons conducted in Yamanashi, Japan, plants of the new *Senecio* differed from plants of the male parent selection in the following characteristics:

1. Plants of the new *Senecio* had larger leaves than plants of the male parent selection.
2. Plants of the new *Senecio* had larger inflorescences than plants of the male parent selection.
3. Plants of the new *Senecio* and the male parent selection differed in ray floret coloration.

Plants of the new *Senecio* can be compared to plants of the cultivar Miss Yokohama, not patented. In side-by-side comparisons conducted in Yamanashi, Japan, plants of the new *Senecio* differed from plants of the cultivar Miss Yokohama in the following characteristics:

1. Plants of the new *Senecio* were taller and more upright than plants of the cultivar Miss Yokohama.
2. Plants of the new *Senecio* were more vigorous than plants of the cultivar Miss Yokohama.
3. Plants of the new *Senecio* had smaller leaves than plants of the cultivar Miss Yokohama.
4. Plants of the new *Senecio* had larger inflorescences than plants of the cultivar Miss Yokohama.
5. Plants of the new *Senecio* flowered for a longer period of time than plants of the cultivar Miss Yokohama.

6. Plants of the new *Senecio* rarely produced seed whereas plants of the cultivar Miss Yokohama typically produced seed.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Senecio*.

The photograph at the top of the sheet comprises a side perspective view of a typical flowering plant of 'Sunsenebulbai'.

The photograph at the bottom of the sheet comprises a close-up view of a typical inflorescence and leaves of 'Sunsenebulbai'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the winter in Yamanashi, Japan, under commercial practice in a glass-covered greenhouse. During the production of the plants, day temperatures ranged from 15 to 30° C. and night temperatures ranged from 13 to 20° C. Plants were about six months from planting into 15-cm containers when the photographs and the description were taken.

Botanical classification: *Senecio cruentus*×*Senecio heritieri* cultivar Sunsenebulbai.

Parentage:

*Female or seed parent.*—*Senecio cruentus* cultivar Jupiter Blue-white, not patented.

*Male or pollen parent.*—Unnamed seedling selection of *Senecio heritieri,* not patented.

Propagation:

*Type.*—Terminal vegetative cuttings.

*Time to initiate roots.*—About one week at 28° C.

*Time to produce a rooted cutting.*—About four weeks at 28° C.

*Root description.*—Fibrous, fleshy, fine and freely branching; light brown in color.

Plant description:

*Appearance.*—Herbaceous potted *Senecio*. Plants compact, upright and outwardly spreading; rounded plant habit. Freely branching with lateral branches potentially developing at every node; dense and full plants. Vigorous growth habit.

*Plant height.*—About 35 cm.

*Plant width.*—About 30 cm.

*Lateral branches.*—Length: About 20 cm. Diameter: About 4.9 mm. Internode length: About 1.7 cm. Texture: Sparsely pubescent. Color: 64A.

*Foliage description.*—Arrangement: Alternate, simple. Length: About 9.2 cm. Width: About 9.8 cm. Shape: Broadly cordate. Apex: Obtuse. Base: Cordate. Margin: Palmately lobed; crenate; slightly undulate. Texture, upper and lower surfaces: Densely pubescent; velvety. Venation pattern: Palmate. Color: Developing and fully expanded foliage, upper surface: 144A; venation, similar to lamina. Developing and fully expanded foliage, lower surface: 146D; venation, similar to lamina. Petiole length: About 8.6 cm. Petiole diameter: About 3.2 mm. Petiole texture, upper and lower surfaces: Smooth. Petiole color, upper and lower surfaces: 64A.

Inflorescence description:

*Appearance.*—Daisy-type composite inflorescences with ray and disc florets developing acropetally on a receptacle. Inflorescences borne on terminals and lateral branches above and beyond the foliage. Slightly fragrant. Typically grown as a natural spray-type.

*Flowering response.*—Long flowering period, under natural conditions, plants flower from late December to May in Japan.

*Postproduction longevity.*—Inflorescences maintain good color and substance for about two weeks. Inflorescences persistent.

*Quantity of inflorescences.*—Freely flowering, about five inflorescences develop per lateral stem.

*Inflorescence bud.*—Height: About 4 mm. Diameter: About 6 mm. Shape: Globose. Color: 130A; towards the base, and apex, close to 79A.

*Spray length.*—About 24 cm.

*Spray diameter.*—About 35 cm.

*Inflorescence size.*—Diameter: About 6.8 cm. Depth (height): About 1 cm. Disc diameter: About 1.6 cm.

*Ray florets.*—Shape: Narrowly elliptic. Orientation: Initially upright; with development, roughly perpendicular to the peduncle. Length: About 2.7 cm. Width: About 1 cm. Apex: Obtuse. Base: Obtuse. Margin: Entire. Texture, upper and lower surfaces: Smooth, glabrous; satiny. Number of ray florets per inflorescence: About 13. Color: When opening and fully opened, upper surface: 93B; towards the base, 155B. When opening and fully opened, lower surface: 93B; towards the base, 155B.

*Disc florets.*—Arrangement: Massed at center of receptacle. Shape: Tubular, fused at base. Apex: Five-pointed; acute. Margin: Entire. Length: About 2.9 mm. Width: About 2.3 mm. Number of disc florets per inflorescence: About 140. Color: 79A becoming closer to 79B with development.

*Phyllaries.*—Length: About 1.5 mm. Diameter: About 1 mm. Shape: Elongated; fused. Apex: Acute. Color, upper and lower surfaces: 139D.

*Peduncles.*—Length: About 3.7 cm. Diameter: About 1.3 mm. Angle: Upright. Strength: Flexible. Texture: Smooth; glabrous. Color: 144B, overlain with 79A.

*Reproductive organs.*—Androecium: Present on disc florets only. Anther length: About 2 mm. Anther color: 79B. Pollen amount: Scarce. Pollen color: 21A. Gynoecium: Present on both ray and disc florets. Pistil length: About 4.7 mm. Stigma shape: Bi-parted. Stigma color: 79B. Style color: 145D. Ovary color: 145C.

*Seed/fruit.*—Seed and fruit production is rarely observed.

Disease/pest resistance: Resistance to pathogens and pests common to *Senecios* has not been observed on plants of the new *Senecio*.

Weather tolerance: Plants of the new *Senecio* have been observed to be resistant to wind, rain and temperatures ranging from about 0 to 30° C.

It is claimed:

1. A new and distinct cultivar of *Senecio* plant named 'Sunsenebulbai', as illustrated and described.

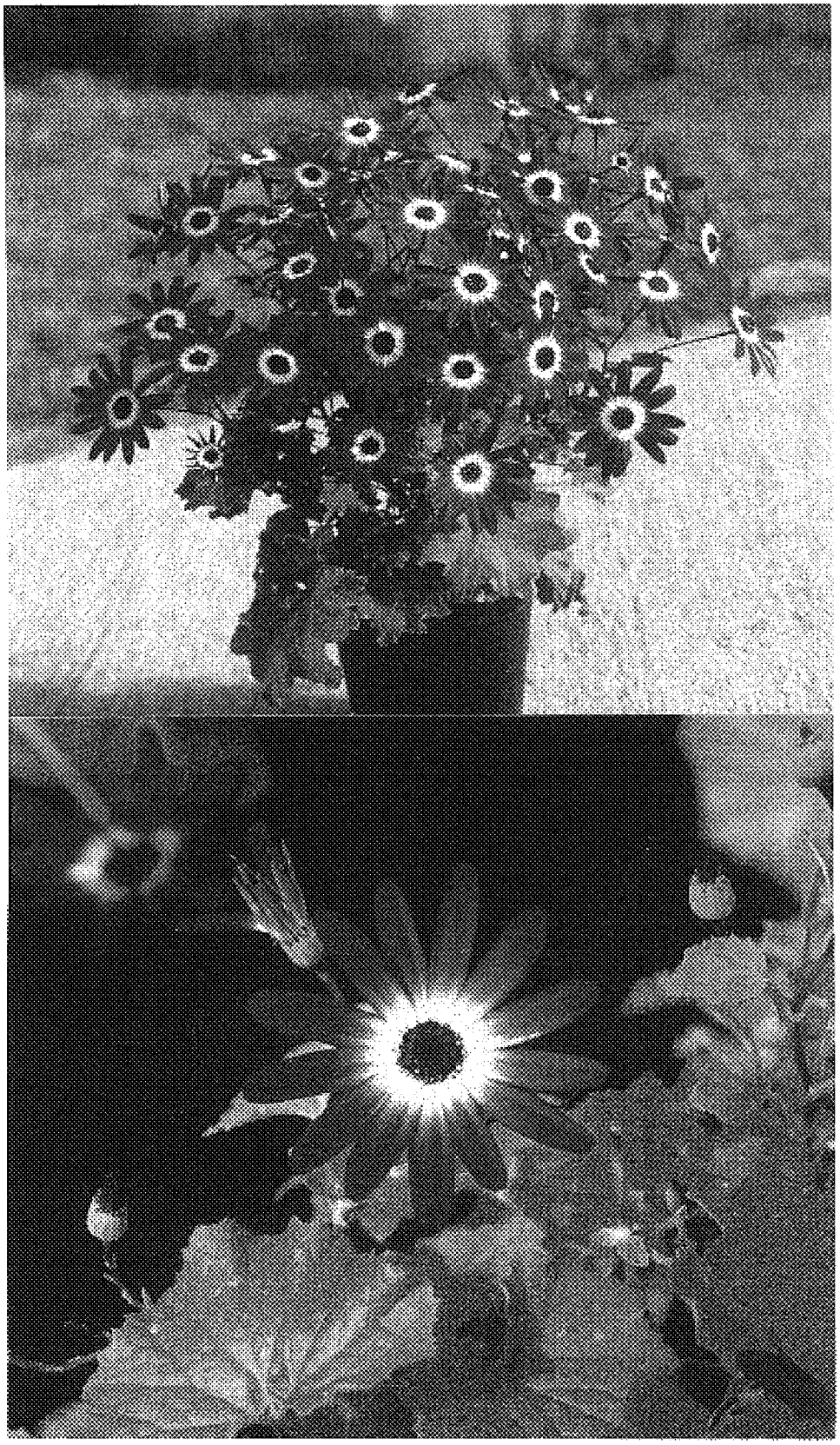

* * * * *